United States Patent [19]

Sage, Jr.

[11] Patent Number: 4,609,286
[45] Date of Patent: Sep. 2, 1986

[54] DISPERSION PRISM FOR SEPARATION OF WAVELENGTHS OF SPECTRALLY RICH LIGHT IN A FLOW CYTOMETRY APPARATUS

[75] Inventor: Burton H. Sage, Jr., Raleigh, N.C.

[73] Assignee: Becton, Dickinson and Company, Franklin Lakes, N.J.

[21] Appl. No.: 600,245

[22] Filed: Apr. 16, 1984

[51] Int. Cl.$^4$ .................. G01N 21/64; G01N 21/27; G01N 21/53

[52] U.S. Cl. .................................. 356/73; 250/461.2; 250/574; 356/39; 356/318; 356/338

[58] Field of Search ............... 356/317, 318, 323, 324, 356/325, 335–338, 73, 39; 250/461.2, 574–576; 324/71.4; 350/286

[56] References Cited

U.S. PATENT DOCUMENTS 2,601,327 6/1952 Rose ..................................... 356/325
3,916,197 10/1975 Fulwyler ..................... 250/461.2 X
4,003,707 1/1977 Lubbers et al. ................. 356/318 X
4,348,107 9/1982 Leif ....................................... 356/72

Primary Examiner—Vincent P. McGraw
Assistant Examiner—Robert D. V. Thompson
Attorney, Agent, or Firm—Richard J. Rodrick

[57] ABSTRACT

A flow cytometry apparatus for determining one or more characteristics of particles or the like flowing in a liquid stream includes a nozzle for generating a liquid flow stream for moving particles therethrough substantially one at a time. A light source provides a spectrally rich beam of light directed toward the particles moving in the stream. A dispersion prism separates the spectrally rich light into a plurality of spatially separated components thereof so as to selectively illuminate the particles with one or more of the separated light components. A detector is included for detecting light with respect to each moving particle and for associating the detected light with one or more characteristics of that particle.

11 Claims, 3 Drawing Figures

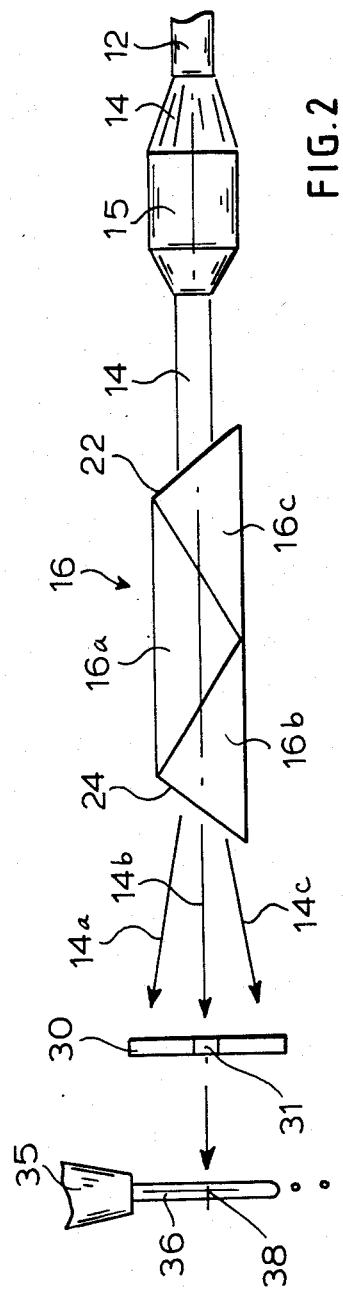
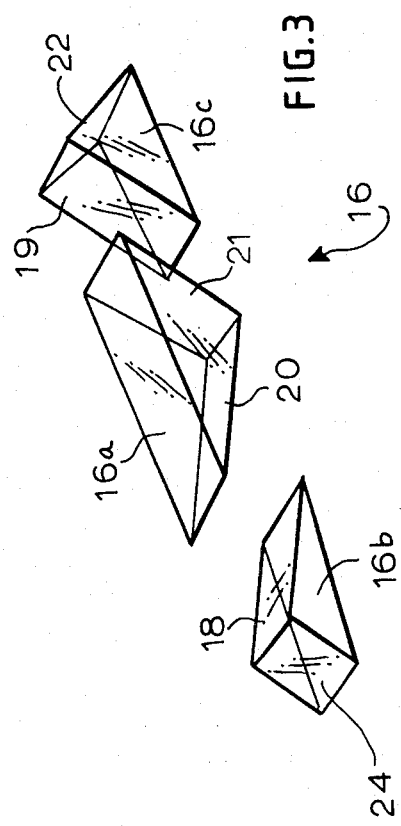

DISPERSION PRISM FOR SEPARATION OF WAVELENGTHS OF SPECTRALLY RICH LIGHT IN A FLOW CYTOMETRY APPARATUS

BACKGROUND OF THE INVENTION

1. Field of the Invention

The present invention relates to a flow cytometry apparatus, and more particularly concerns a flow cytometry apparatus for detemining characteristics of cells or the like which provides for spatial wavelength separation of spectrally rich light for improved excitation energy in a flow cytometry apparatus.

2. Description of the Prior Art

Flow cytometry apparatuses rely upon the flow of cells or other particles in a liquid flow stream in order to determine one or more characteristics of the cells under investigation. For example, a liquid sample containing cells is directed through the flow cytometry apparatus in a rapidly moving liquid stream so that each cell passes serially, and substantially one at a time, through a sensing region. Cell volume may be determined by changes in electrical impedance as each cell passes through the sensing region. Similarly, if an incident beam of light is directed at the sensing region, the passing cells scatter such light as they pass therethrough. This scattered light has served as a function of cell shape, index of refraction, opacity, roughness and the like. Further, fluorescence emitted by labeled cells which have been excited as a result of passing through the excitation energy of the incident light beam is detectable for identification of specifically labeled cells. Not only is cell analysis performed on the flow cytometry apparatuses, but sorting of cells may also be achieved. Lasers have been used as the source of the incident beam of illumination in flow cytometry apparatuses, as well as sources of incoherent or non-collimated light, such as mercury or xenon arc lamps, which typically provide spectrally rich light. Such apparatuses which include incoherent light sources have been described in copending patent applications, Ser. No. 276,738, filed on June 24, 1981, in the U.S. Patent and Trademark Office, and Ser. No. 482,346, filed in the U.S. Patent and Trademark Office on Apr. 5, 1983, both applications having a common assignee herewith, and also in U.S. Pat. No. 4,348,107. One flow cytometry apparatus known and sold as the FACS TM Analyzer, FACS Systems, Becton, Dickinson and Company, Sunnyvale, California, presently relies upon a mercury arc lamp as the excitation source of incoherent light for illuminating the stream of particles or cells flowing therethrough.

Excitation energy from a mercury or xenon arc lamp, or other incoherent light sources, is typically bright and spectrally rich. Accordingly, these arc lamps are desirable sources of excitation energy since the spectrally rich light is composed of a group of very intense lines (wavelengths at which the energy is much higher than at other wavelengths). Ordinarily, these energy lines are selected by using optical filters which either absorb or reflect the light of the undesirable wavelengths. By utilization of this filtering technique, the intense energy lines of light are permitted to intercept the flowing stream of particles or cells in the flow cytometry apparatus. If the cells have been labeled with a fluorochrome, the intense energy lines serve as the excitation energy to cause the fluorescently labeled cells to emit fluorescence. While the known filters are efficient in removing undesirable wavelengths of light in this type of illumination scheme, the filters usually attenuate the desired wavelengths of light by up to 70%. Moreover, the filters need to be changed each time a different wavelength is selected, for example, as the excitation energy for the fluorescently labeled cells.

Accordingly, improvements are still being sought for flow cytometry apparatuses which rely upon an incoherent light source, such as mercury or xenon arc lamps which provide spectrally rich light for illumination of the particles flowing in the liquid flow stream. Improvements are needed particularly to selectively choose those desired wavelengths or lines relied upon for excitation energy for the fluorescently labeled cells. It is to such improvement that the present invention is directed.

SUMMARY OF THE INVENTION

The flow cytometry apparatus of the present invention for determining one or more characteristics of particles or the like flowing in a liquid stream comprises means for moving particles, substantially one at a time, in a liquid flow stream. Means provides a spectrally rich beam of light directed toward the particles moving in the stream. Means separates the spectrally rich light into a plurality of spatially separated components thereof for selectively illuminating the particles with one or more of the separated light components. Means for detecting light with respect to each moving particle is included, which also associates the detected light with one or more characteristics of such particle.

In a preferred embodiment of the present invention, an arc lamp provides the light energy, as a beam of incoherent light, for illumination of the particles or cells moving in the flow stream. The means to separate the light into spatially separated components or wavelengths is preferably a light transmissive dispersion prism. This prism is formed from a plurality of smaller prisms and made from different materials. The prism is positioned in the path of the light beam between the arc lamp and the flow stream. It is the function of this prism to spatially separate incoherent light comprised of a spectrum of wavelengths into a plurality of wavelength components thereof and to direct the spatially separated components in different directions. As a result, one or more of the components of light selectively illuminate the cells flowing in the flow stream. An adjustable light barrier with a slit therethrough is preferably positioned between the dispersion prism and the flow stream. This barrier selectively blocks some components of separated light and selectively allows at least one separated component of light to pass through the slit to illuminate the cells in the flow stream.

In accordance with the principles of the present invention, filterless wavelength separation of spectrally rich light emanating from the light source, such as an arc lamp, is accomplished. Instead of relying upon optical filters to either absorb or reflect light of undesirable wavelengths, a dispersion prism is employed in the present invention. The image of the arc from the arc lamp is imaged through the dispersion prism. As a result, the image of the arc at the image plane exists at positions dependent upon the wavelength of the emitted light. Different wavelengths within the originally spectrally rich light are thus separated spatially since the wavelength images exist at different positions at a focal plane. Once spatial separation of wavelengths occurs, the excitation energy for the flow cytometry apparatus may be selected by placing a slitted barrier at this focal plane. Only the desired wavelengths of light pass through the slit for subsequent refocusing on the cells flowing in the liquid stream. Furthermore, the light transmission through the dispersion prism is advantageously high at those wavelengths normally used in flow cytometry apparatuses. It is not unusual to have a transmission efficiency above 80%. Still further, in order to select different desired wavelengths for the excitation energy, either an adjustment of the slit or the arc lamp/dispersion prism is sufficient to accomplish this result. This relatively straight-forward adjustment obviates the need to replace any components, which is the case when using optical filters for wavelength selection.

BRIEF DESCRIPTION OF THE DRAWINGS

FIG. 1 is a schematic illustration of a preferred embodiment of the optical elements and light paths of a flow cytometry apparatus of the present invention for determining one or more characteristics of cells or the like;

FIG. 2 is an enlarged schematic representation of the preferred dispersion prism embodied in a flow cytometry apparatus, further depicting the wavelength separation feature; and FIG. 3 is an exploded perspective view of the dispersion prism of FIG. 2 illustrating the smaller prisms which comprise the dispersion prism.

DETAILED DESCRIPTION

Figure 1:
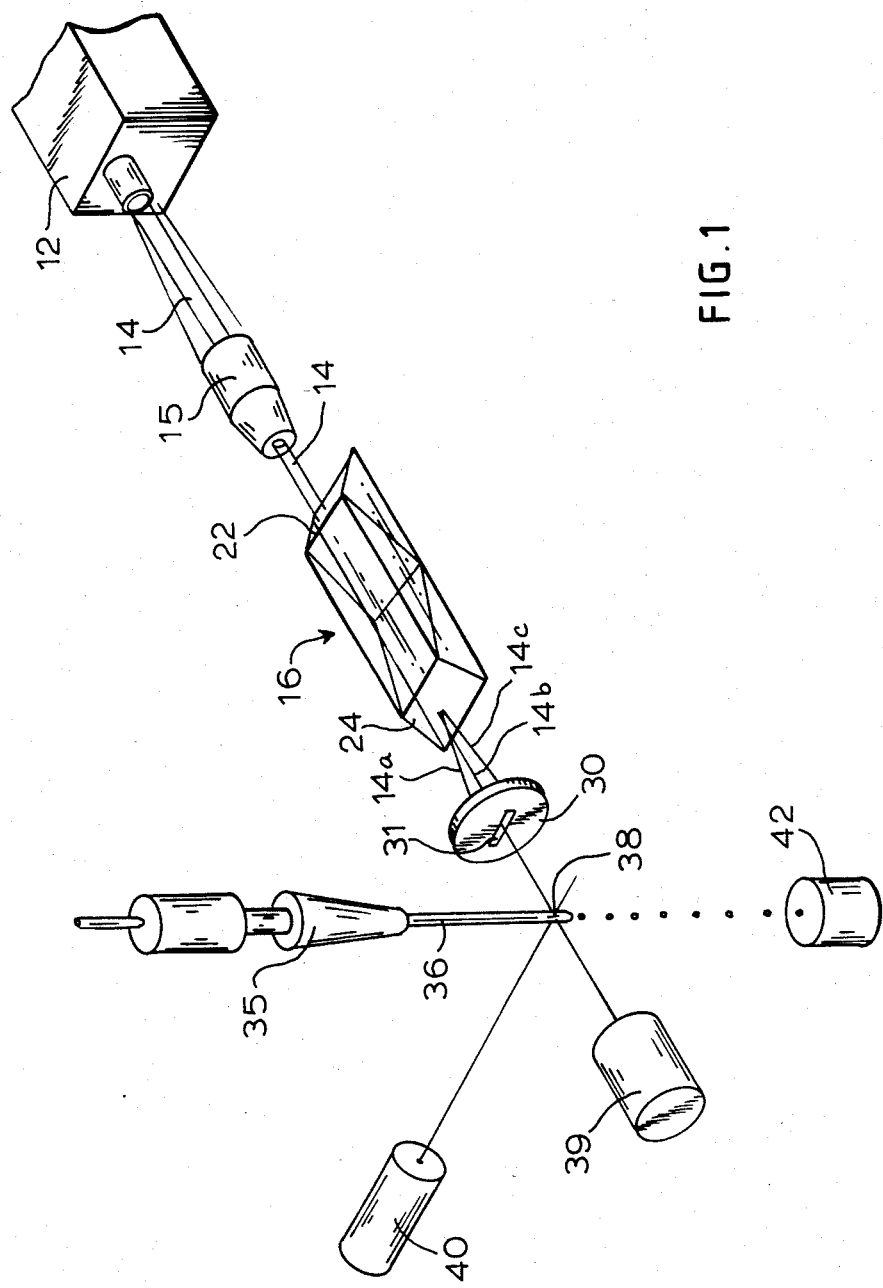

While this invention is satisifed by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Adverting to the drawings and FIG. 1 in particular, the optical and particle flow elements of a flow cytometry apparatus 10 are illustrated. The optical and flow elements of FIG. 1 represent the major components of a flow cytometry apparatus for moving particles, such as cells or the like, in a liquid stream, substantially one at a time, in order to assess those particles for specific characteristics thereof. For example, the elements of FIG. 1 may be included in a FACS TM cell analyzer, manufactured and sold by the FACS Systems Division of Becton, Dickinson and Company, Sunnyvale, Calif. The FACS TM cell analyzer assesses cell populations and subpopulations on the basis of volume, light scatter and fluorescence, or combinations thereof, in a wide variety of research laboratory applications. In addition to the optical and flow elements to be described in more detail herein, and which may be embodied in an instrument such as the FACS TM analyzer, other details of such cell analyzer useful in conjunction with the present invention are described in the aforementioned patent applications, assigned in common with the present assignee. It is understood that the present invention is useful in many different types of flow cytometry or flow fluorometric apparatuses, whether measuring light scatter, particle volume, fluorescence or other optical parameters for the identification or quantification of cells or the like in a sample liquid medium. The optical elements in particular, of the present invention represent the essence of the improvement in flow cytometry apparatuses such as described in the aforementioned patent applications.

As illustrated in FIGS. 1 and 2, light energy is provided for the present flow cytometry apparatus by a light source 12 which provides an incoherent beam of light comprising a broad or rich spectrum of wavelengths. An arc lamp, such as a mercury or xenon arc lamp, is the preferred light source of the present invention.

Excitation energy is provided in flow cytometry apparatus 10 by a beam of spectrally rich light 14 produced by light source 12. Typically, the beam of light is directed to a condenser lens 15 for focusing the beam of light. From condenser lens 15, the light beam is directed to dispersion prism 16. It is appreciated that the light which enters dispersion prism 16, when generated by a light source such as an arc lamp, has a wide spectrum of wavelengths, covering different color regions of the color spectrum as well as scattered light, background light and the like. Inasmuch as it is desirable to transmit the intense lines of light, i.e. wavelengths at which the energy is higher than at other wavelengths, dispersion prism 16 acts as an optical filter to subsequently block or prevent the passage of undesirable wavelengths or extraneous light signals while permitting the transmission of certain, preselected wavelengths primarily associated with the intense lines of light energy.

As illustrated in all of the drawing figures, light transmissive dispersion prism 16 is preferably formed from a plurality of smaller prisms 16a,b and c, as shown in detail in FIG. 3. When these smaller prisms are positioned together so that the angular faces 18 and 19 of prisms 16b and 16c, respectively, contact angular faces 20 and 21 of prism 16a, it can be seen that dispersion prism 16 has a relatively elongate longitudinal axis. The smaller prisms are preferably held in contact by a thin layer of transparent cement or by other practicable, functional techniques. As an assembled unit, dispersion prism 16 includes side surfaces, i.e., those wall surfaces extending substantially parallel to the axis of light beam 14, whereas end surfaces 22 and 24 are transmissive to light. Further, in order to improve the efficiency of the light transmission therethrough, end surfaces 22 and 24 are preferably treated with an anti-reflectance agent. Moreover, in order to facilitate the spatial separation of wavelengths of light and direct those separated wavelengths in different directions, it is preferred that end surfaces 22 and 24 of dispersion prism 16 be angularly positioned with respect to the axis of the incident light beam entering the dispersion prism. It is understood that this preferred angularity of the end surfaces of the dispersion prism may be varied according to many factors including the wavelengths of interest, the materials of the dispersion prism, the relative directions that wavelengths will take after spatial separation, and the like.

So that spectrally rich light entering end surface 22 of the dispersion prism will be spatially separated into different wavelengths or components of light, it is preferred that smaller prisms 16a,b and c be made of different materials capable of transmitting light therethrough. For example, smaller prism 16a may be fabricated from a dense flint, whereas smaller prisms 16b and 16c may both be fabricated from fluorite or light crowns. Different combinations of light transmissive materials may be employed so as to assure the refraction of different wavelengths of light in different directions. Further, while triangularly shaped smaller prisms are illustrated particularly in FIG. 3, it is understood that the various faces of the prisms may be angled or shaped differently in order to facilitate the wavelength separation as described herein. As a result of the characteristics and properties of dispersion prism 16, spectrally rich light beam 14 is separated into light components each comprised of wavelengths in a more narrowly defined range. Exemplary components of light exiting the dispersion prism in different directions are designated by numerals 14a, 14b and 14c.

These spatially separated components of light permit the user to select or reject wavelengths of interest. In order to select or reject portions of the light spectrum which pass through dispersion prism 16, an adjustable light barrier 30 is positioned in the light path. A slit 31 extends through the barrier so that the desired light component, 14a,b or c may pass therethrough. It is understood that additional slits would pass additional desired wavelengths of light in beam 14. Wavelengths that are undesirable are blocked by preventing those wavelengths from passing through slit 31 inasmuch as barrier 30 is preferably a light absorbing member. To permit other wavelengths to pass, barrier 30 may be selectively adjusted so that the slit(s) is (are) aligned with the wavelength exiting dispersion prism 16 in a different direction.

Separated light components 14a,b and c, subsequent to passing through slit 31, whether individually or at the same time, are directed to the particles or cells flowing in the flow stream. To this end, a nozzle 35, incorporated within the flow cytometry apparatus of the present invention, facilitates the flowing of cells or particles within liquid stream 36. The utilization of a nozzle of this type is well-known and is described, for example, in U.S. Pat. No. 3,826,364. As each cell or particle passes through the illuminated light region 38, where one of the spatially separated components of light beam 14 intersects liquid stream 36, light scattered thereby may be detected by an appropriate photodetector 39. Similarly, fluorescence, if emitted by cells energized by the illumination from the light source, may also be detected. Typically, fluorescence emitted by the flowing cells is detected substantially at a right angle to the axis of light beam 14. One or more fluorescence detectors 40 may be utilized to detect fluorescence emitted by the energized cells. Inasmuch as the energy for activating the fluorochromes on fluorescently labeled cells is provided by illumination at a certain wavelength, the present invention is well adapted to serve this need by spatially separating the wavelengths of interest. Photodetector 39 and fluorescence detector 40 may be well-known photomultiplier tubes or similar devices which convert light signals into electrical impulses so that the light thereby detected can be associated with the cells responsible for such light signals. The electrical signals from the various detectors are typically fed to the electronics (not shown) of the apparatus for purposes of display, storage or further processing so that one or more characteristics of cells under analysis can be determined.

Particles or cells in liquid stream 36 may be collected in an appropriate container 42, or perhaps, may be sorted and collected in different containers if the flow cytometry apparatus employs a sorting capability.

Thus, the present invention provides the filterless, spatial separation of wavelengths particularly useful for separating wavelengths from a spectrally rich light source in a flow cytometry apparatus. Rather than reliance upon optical filters, the preferred dispersion prism herein spatially separates wavelengths into different directions. Therefore, some of the wavelengths may be selected for excitation energy of the flowing cells, particularly when those cells have been fluorescently labeled. Undesirable wavelengths or extraneous light signals are readily rejected and absorbed without the need for optical filters. Light transmission through the dispersion prism is exceptionally high thereby magnifying the advantageous features of the present invention.

What is claimed is:

1. A flow cytometry apparatus for determining characteristics of cells or the like flowing in a liquid stream comprising:
    means for moving cells, substantially one at a time, in a liquid flow stream;
    an excitation light source for providing a beam of spectrally rich light directed toward said cells moving in said flow stream;
    a light transmissive dispersion prism, positioned in the path of said light beam between said source and said flow stream, capable of spatially separating said spectrally rich light into a plurality of wavelength components thereof and directing said separated components in different directions so that one or more of said components may selectively illuminate said cells moving in said flow stream, said dispersion prism having a plurality of smaller light transmissive prisms arranged in contact with each other along a relatively elongate longitudinal axis;
    a light barrier with a slit therethrough, positioned in the light path between said dispersion prism and said flow stream, for blocking some components of separated light and for allowing at least one spatially separated component of light to pass through said slit for illuminating the cells in said flow stream, said light barrier being a light absorbing member to absorb light striking same, said slit being aligned with said at least one spatially separated component of light which exits said prism to permit said component to pass through said barrier;
    means for detecting light associated with each moving cell as it passes through said area of illumination; and
    means for using said detected light to determine one or more characteristics of said cells.

2. The apparatus of claim 1 wherein the end surfaces of said dispersion prism are angularly positioned with respect to the axis of the incident light entering said prism.

3. The apparatus of claim 1 wherein the end surfaces of said prism are treated with anti-reflectance agent to improve efficiency of light transmission therethrough.

4. The apparatus of claim 1 which further includes a lens positioned in the light path between said light source and said dispersion prism for focusing light into said dispersion prism.

5. The apparatus of claim 1 wherein said light barrier is configured to selectively permit different separated light components to pass through its slit.

6. The apparatus of claim 5 wherein said light barrier is adjustable to selectively permit different separated light components to pass through its slit.

7. The apparatus of claim 1 wherein at least one of the smaller prisms is made of a dense flint and at least another of said smaller prisms is made of light crown.

8. The apparatus of claim 1 wherein said means for detecting light includes a device for detecting fluorescence emitted by the cells passing through said area of illumination.

9. The apparatus of claim 1 wherein said means for detecting light includes a device for detecting light scattered by the cells passing through said area of illumination.

10. A flow cytometry apparatus for determining characteristics of cells or the like flowing in a liquid stream comprising:

means for moving cells, substantially one at a time, in a liquid flow stream;

an arc lamp for providing a beam of spectrally rich light to illuminate said cells moving in said flow stream;

a light transmissive dispersion prism formed from a plurality of smaller prisms made from different materials arranged in contact with each other along a relatively elongate longitudinal axis and positioned in the path of said light beam between said lamp and said flow stream and capable of spatially separating said light comprised of a spectrum of wavelengths into a plurality of components thereof and directing said spatially separated components in different directions so that one or more of said components may selectively illuminate said cells flowing in said stream;

a lens positioned in the light path between said lamp and said dispersion prism for focusing said spectrally rich light into said dispersion prism;

an adjustable light barrier with a slit therethrough, positioned between said dispersion prism and said flow stream, for selectively blocking some components of separated light and for selectively allowing at least one separated component of light to pass through said slit to illuminate the cells in said flow stream, said light barrier being a light absorbing member to absorb light striking same, said slit being alignable with said at least one separated component of light which exits said prism to permit said component to pass through said barrier;

means for detecting light associated with each moving cell as it passes through said area of illumination; and means for using said detected light to determine one or more characteristics of said cells.

11. The apparatus of claim 10 wherein said arc lamp is a mercury arc lamp.

* * * * *